United States Patent
Yoshida et al.

(10) Patent No.: US 9,579,309 B2
(45) Date of Patent: Feb. 28, 2017

(54) PROPHYLACTIC OR THERAPEUTIC AGENT FOR POSTERIOR OCULAR DISEASE CONTAINING TETRAHYDROPYRANYLAMINOCYCLO-PENTYLCARBONYLTETRAHYDRO-PYRIDOPYRIDINE DERIVATIVE AS EFFECTIVE INGREDIENT

(71) Applicant: SANTEN PHARMACEUTICAL CO., LTD., Osaka-shi, Osaka (JP)

(72) Inventors: Atsushi Yoshida, Ikoma (JP); Sae Akao, Ikoma (JP); Shinji Yoneda, Ikoma (JP); Komei Okabe, Osaka (JP); Tomomi Kohara, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/771,261

(22) PCT Filed: Feb. 27, 2014

(86) PCT No.: PCT/JP2014/054852
§ 371 (c)(1),
(2) Date: Aug. 28, 2015

(87) PCT Pub. No.: WO2014/133072
PCT Pub. Date: Sep. 4, 2014

(65) Prior Publication Data
US 2016/0008333 A1    Jan. 14, 2016

(30) Foreign Application Priority Data

Feb. 28, 2013 (JP) ................................ 2013-038703

(51) Int. Cl.
*A61K 31/4375* (2006.01)
(52) U.S. Cl.
CPC ................................ *A61K 31/4375* (2013.01)
(58) Field of Classification Search
CPC .......................... A61K 31/4375; C07D 471/04
USPC ......................................... 546/122; 514/300
See application file for complete search history.

(56) References Cited

U.S. PATENT DOCUMENTS

2007/0135474 A1    6/2007    Jensen et al.

FOREIGN PATENT DOCUMENTS

| JP | 2007-509940 A | 4/2007 |
| WO | WO 03/092586 A1 | 11/2003 |
| WO | WO 2005/044264 A1 | 5/2005 |
| WO | WO 2012/094703 A1 | 7/2012 |

OTHER PUBLICATIONS

New Illustrated Handbook of Clinical Ophthalmology, vol. 5 "Vitreoretinal disease", pp. 184-189, 232-237 (2000)—17 pages (including English translation).
Xia M et al.: "Recent Developments in CCR2 Antagonists," Expert Opinion on Therapeutic Patents, Informa Healthcare, GB, vol. 19, No. 3, Mar. 1, 2009, pp. 295-303.
Extended Search Report issued by the European Patent Office in corresponding European Patent Application No. 14757577.3 on Aug. 3, 2016 (6 pages).
International Search Report (PCT/ISA/210) mailed on Apr. 8, 2014, by the Japanese Patent Office as the International Searching Authority for International Application No. PCT/JP2014/054852.
Written Opinion (PCT/ISA/237) mailed on Apr. 8, 2014, by the Japanese Patent Office as the International Searching Authority for International Application No. PCT/JP2014/054852.
Ping Xie et al., "Suppression and Regression of Choroidal Neovascularization in Mice by a Novel CCR2 Antagonist, INCB3344", Plos ONE, Dec. 2011, vol. 6, Issue 12, pp. 1-10.
Athanasios Dagkalis et al., "Development of Experimental Autoimmune Uveitis: Efficient Recuitment of Monocytes Is Independent of CCR2", Invest. Ophthalmol. Vis. Sci., Sep. 2009, vol. 50, No. 9, pp. 4288-4294.
Stephen J. Ryan et al., Journal of Japanese Ophthalmological Society, 103, pp. 923-947, Dec. 1999.
New Illustrated Handbook of Clinical Ophthalmology, vol. 5 "Vitreoretinal disease", pp. 184-189, 232-237 (2000).
Alaa S. Awad et al., "Monocyte/Macrophage Chemokine Receptor CCR2 Mediates Diabetic Renal Injury", Am. J. Physiol. Renal Physiol., vol. 301, pp. F1358-F1366, Aug. 31, 2011.
Dong Yang et al., "Roles of CC Chemokine Receptors (CCRs) on Lipopolysaccharide-Induced Acute Lung Injury", Respiratory Physiology Neurobiology, vol. 170, pp. 253-259, (2010).

*Primary Examiner* — Niloofar Rahmani
(74) *Attorney, Agent, or Firm* — Buchanan, Ingersoll & Rooney PC

(57) ABSTRACT

The present invention relates to a prophylactic or therapeutic agent for a posterior ocular disease containing the compound represented by a formula (1), its enantiomer or diastereomer, or their pharmaceutically acceptable salt thereof as an active ingredient.

5 Claims, No Drawings

PROPHYLACTIC OR THERAPEUTIC AGENT FOR POSTERIOR OCULAR DISEASE CONTAINING TETRAHYDRO-PYRANYLAMINOCYCLOPENTYLCARBONYL-TETRAHYDROPYRIDOPYRIDINE DERIVATIVE AS EFFECTIVE INGREDIENT

TECHNICAL FIELD

The present invention relates to a prophylactic or therapeutic agent for a posterior ocular disease containing a tetrahydropyranylaminocyclopentylcarbonyltetrahydropyridopyridine derivative as an active ingredient.

BACKGROUND ART

The posterior ocular disease generally means a disease at the vitreous body, the retina, the choroid, the sclera or the optic nerve, and these diseases are deeply involved with neovascular expression or vascular permeability enhancement. That is, in the posterior ocular diseases such as age-related macular degeneration, diabetic retinopathy, diabetic macular edema, retinal vein occlusion, uveitis, etc., it has been known that neovascular expression or enhancement of vascular permeability is a main factor of formation of the pathological condition and progress of the pathological condition, so that it is useful for the treatment of these diseases to inhibit neovascularization, or to suppress vascular permeability enhancement (Non-Patent Document 1 and Non-Patent Document 2).

On the other hand, chemokine is a physiologically active protein which mainly acts on an immune system in vivo, and at present, substances exceeding 50 kinds have been revealed, which can be classified into four of C, CC, CXC, and CX3C based on the structural differences of the common cysteine in the amino acid sequence. The respective chemokines bind to GPCR (G protein-coupled receptor) and show their physiological actions, and in particular, the receptor to which MCP-1 being a CC chemokine binds, is called as CCR2.

In Non-Patent Document 3 and Non-Patent Document 4, there are disclosed that RS-504393 which is a CCR2 receptor antagonist has a protective effect onto nephropathy or endotoxin-induced pneumonopathy of diabetes model mouse.

Also, in Patent Document 1, there is disclosed that a tetrahydropyranylaminocyclopentylcarbonyltetrahydropyridopyridine derivative which controls an activity of a chemokine receptor such as a CCR2 receptor, etc., and synthetic examples of a plural number of tetrahydropyranylaminocyclopentylcarbonyltetrahydropyridopyridine derivatives are described. In addition, it has been disclosed that the tetrahydropyranylaminocyclopentylcarbonyltetrahydropyridopyridine derivative is useful for prophylaxis or treatment of inflammatory and immunoregulatory disorders and diseases, an allergic disease, atopic conditions (allergic rhinitis, dermatitis, conjunctivitis and asthma, etc.) and autoimmune diseases such as rheumatoid arthritis and atherosclerosis, etc.

Also, in Patent Document 2, ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine succinate which is one of the tetrahydropyranylaminocyclopentylcarbonyltetrahydropyridopyridine derivative has been disclosed, and shown to be a CCR2 receptor antagonist.

However, there is neither described nor suggested in Patent Documents 1 and 2, and Non-Patent Documents 1, 2, 3 and 4 about the effects exerted on the posterior ocular disease by the tetrahydropyranylaminocyclopentylcarbonyltetrahydropyridopyridine derivative, in particular, a compound represented by the formula (1):

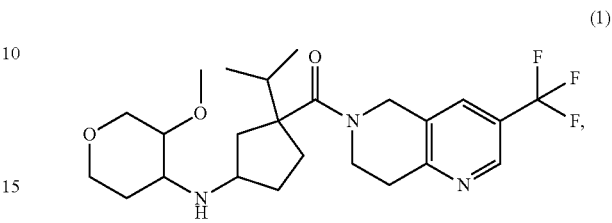

(1)

its enantiomer or diastereomer, or their pharmaceutically acceptable salts.

PRIOR ART DOCUMENTS

Patent Documents

Patent Document 1: WO 2003/092586A
Patent Document 2: WO 2005/044264A

Non-Patent Documents

Non-Patent Document 1: Journal of Japanese Ophthalmological Society, 103, pp. 923-947 (1999)
Non-Patent Document 2: New Illustrated Handbook of Clinical Ophthalmology, vol. 5 "Vitreoretinal disease", pp. 184-189, 232-237 (2000)
Non-Patent Document 3: Am. J. Physiol. Renal Physiol. 301: F1358-1366 (2011)
Non-Patent Document 4: Respir. Physiol. Neurobiol. 170: pp. 253-259 (2010)

DISCLOSURE OF THE INVENTION

Problems to be Solved by the Invention

An object of the present invention is to provide a prophylactic or therapeutic agent for a posterior ocular disease which contains a tetrahydropyranylaminocyclopentylcarbonyltetrahydropyridopyridine derivative as an active ingredient.

Means to Solve the Problems

The present inventors have intensively studied to search a novel prophylactic or therapeutic agent for a posterior ocular disease containing a tetrahydropyranylaminocyclopentylcarbonyltetrahydropyridopyridine derivative as an active ingredient, and as a result, they have found that a compound represented by the formula (1):

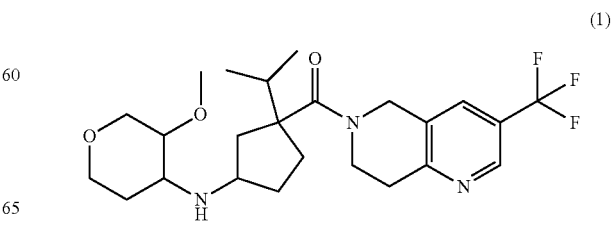

(1)

its enantiomer or diastereomer, or their pharmaceutically acceptable salts have excellent inhibitory activity on angiogenesis and suppressive activity on vascular hyperpermeability at the posterior ocular tissue such as the retina and the choroid, whereby they have accomplished the present invention.

The present invention relates to the following.

The present invention relates to a prophylactic or therapeutic agent for a posterior ocular disease, which comprises a compound represented by the following formula (1):

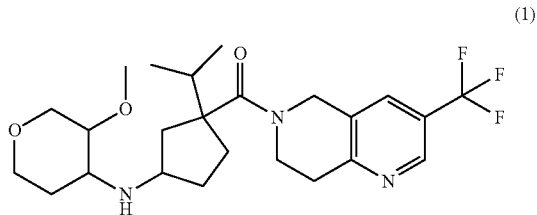 [SMILES: COC1COCCC1NC1CCC(C(=O)N2CCc3ncc(C(F)(F)F)cc3C2)(C(C)C)C1]

(1)

its enantiomer or diastereomer, or their pharmaceutically acceptable salt thereof as an active ingredient.

Also, other embodiments of the present invention relate to a prophylactic or therapeutic agent for a posterior ocular disease, which comprises a compound represented by the formula (1a):

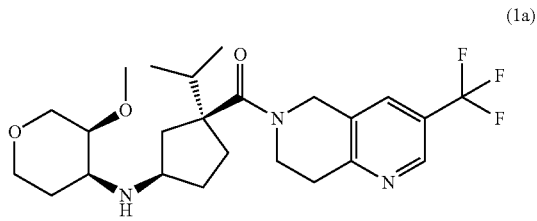 [SMILES: CO[C@@H]1COCC[C@@H]1N[C@@H]1CC[C@@](C(=O)N2CCc3ncc(C(F)(F)F)cc3C2)(C(C)C)C1]

(1a)

or its pharmaceutically acceptable salt as an active ingredient.

Further, other embodiments of the present invention relate to the prophylactic or therapeutic agent for a posterior ocular disease wherein the pharmaceutically acceptable salt of the compound represented by the above-mentioned formula (1) or (1a) is a succinate.

Moreover, other embodiments of the present invention relate to the prophylactic or therapeutic agent for a posterior ocular disease containing the above-mentioned compound as an active ingredient which is a prophylactic or therapeutic agent, wherein the posterior ocular disease is a disease at the vitreous body, the retina, the choroid, the sclera or the optic nerve.

Furthermore, other embodiments of the present invention relate to the prophylactic or therapeutic agent for a posterior ocular disease containing the above-mentioned compound as an active ingredient which is a prophylactic or therapeutic agent, wherein the posterior ocular disease is a posterior ocular disease to which a CCR2 receptor pertains.

Also, other embodiments of the present invention relate to the prophylactic or therapeutic agent for a posterior ocular disease containing the above-mentioned compound as an active ingredient which is a prophylactic or therapeutic agent, wherein the posterior ocular disease is at least one selected from the group consisting of age-related macular degeneration, diabetic retinopathy, diabetic macular edema, retinal pigmentary degeneration, proliferative vitreoretinopathy, retinal artery occlusion, retinal vein occlusion, uveitis, Leber's disease, retinopathy of prematurity, retinal detachment, retinal pigment epithelial detachment, central serous chorioretinopathy, central exudative chorioretinopathy, polypoidal choroidal vasculopathy, multiple choroiditis, neovascular maculopathy, retinal aneurysm, retinal angiomatous proliferation, ophthalmic nerve disorder caused by these diseases, ophthalmic nerve disorder caused by glaucoma and ischemic ophthalmic nerve disorder.

Further, other embodiments of the present invention relate to the prophylactic or therapeutic agent for a posterior ocular disease containing the above-mentioned compound as an active ingredient which is a prophylactic or therapeutic agent, wherein the posterior ocular disease is at least one selected from the group consisting of age-related macular degeneration, diabetic retinopathy, diabetic macular edema, retinal vein occlusion and uveitis.

Moreover, other embodiments of the present invention relate to the prophylactic or therapeutic agent for a posterior ocular disease containing the above-mentioned compound as an active ingredient which is a prophylactic or therapeutic agent, wherein an administration form is instillation administration, intravitreal administration, subconjunctival administration, administration to the interior of the conjunctival sac, administration under the Tenon's capsule or oral administration.

Furthermore, other embodiments of the present invention relate to the prophylactic or therapeutic agent for a posterior ocular disease containing the above-mentioned compound as an active ingredient which is a prophylactic or therapeutic agent, wherein a dosage form is an eye drop, an ophthalmic ointment, an intercalating agent, a plaster, an injection, a tablet, a fine granule or a capsule.

In addition, the present invention relates to the following.

The other embodiments of the present invention relate to a use of the compound represented by the above-mentioned formula (1) in a prophylaxis or treatment for a posterior ocular disease.

Also, other embodiments of the present invention relate to a use of the compound represented by the above-mentioned formula (1) for the manufacture of a medicine of a prophylaxis or treatment for a posterior ocular disease.

Further, other embodiments of the present invention relate to a pharmaceutical composition for a prophylaxis or treatment of a posterior ocular disease comprising a therapeutically effective amount of the compound represented by the above-mentioned formula (1) and an additive.

Moreover, other embodiments of the present invention relate to a method for a prophylaxis or treatment of a posterior ocular disease which method comprises administering an effective amount of the compound represented by the above-mentioned formula (1).

Effects of the Invention

The prophylactic or therapeutic agent for a disease containing the compound represented by the above-mentioned formula (1) as an active ingredient is useful as a prophylactic or therapeutic agent for a posterior ocular disease.

BEST MODE TO CARRY OUT THE INVENTION

In the following, the present invention is explained in detail.

The compound contained in the prophylactic or therapeutic agent for a posterior ocular disease of the present invention can be prepared according to the usual manner in the field of the organic synthetic chemistry. For example, it can be prepared according to the method disclosed in WO 2003/092586A and WO 2005/044264A, etc. In addition, a geometric isomer (cis-trans isomers), an optical isomer (an enantiomer, a diastereomer) or a tautomer of the compound can be isolated and purified by the usual manner such as column chromatography, HPLC, etc.

The compound contained in the prophylactic or therapeutic agent for a posterior ocular disease of the present invention is a compound represented by the formula (1):

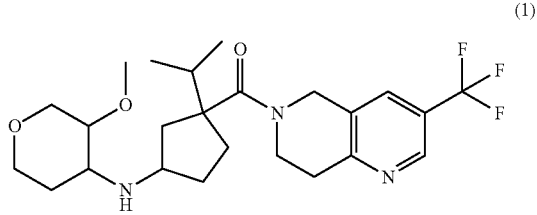 [SMILES: COC1COCCC1NC1CCC(C(=O)N2CCc3ncc(C(F)(F)F)cc3C2)(C(C)C)C1]

(1)

its enantiomer or diastereomer, or their pharmaceutically acceptable salts.

When a geometric isomer (cis-trans isomers), an optical isomer (an enantiomer, a diastereomer) or a tautomer is present in the compound represented by the above-mentioned formula (1), these are also contained in the scope of the compound represented by the formula (1). In addition, the compound represented by the formula (1) may be a mixture of one or two or more isomers selected from the group consisting of the geometric isomer (the cis-trans isomers), the optical isomer (the enantiomer, the diastereomer) and the tautomer.

The "pharmaceutically acceptable salt" of the compound represented by the above-mentioned formula (1) may be mentioned, for example, a salt with an inorganic acid or a salt with an organic acid. The inorganic acid may be mentioned, for example, hydrochloric acid, hydrobromic acid, hydroiodic acid, nitric acid, sulfuric acid, phosphoric acid, etc. The organic acid may be mentioned, for example, acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, sulfosalicylic acid, etc., and succinic acid is preferred.

The compound represented by the above-mentioned formula (1) may take a form of a hydrate or a solvate.

When crystal polymorphism and a crystal polymorphism group (crystal polymorphism system) exist in the compound represented by the above-mentioned formula (1), these crystal polymorphs and crystal polymorphism group (crystal polymorphism system) are also included in the scope of the compound of the present invention. Here, the crystal polymorphism group (crystal polymorphism system) means a crystal form at the respective stages when the crystal form is variously changed by the conditions and states of preparation, crystallization, preservation, etc., of these crystals (incidentally, the state after preparation is also contained in the above states), and the whole processes.

In the following, the compound represented by the above-mentioned formula (1), its enantiomer or diastereomer, or their pharmaceutically acceptable salts are also referred to as "the compounds of the present invention (1)".

Examples of the compounds represented by the above-mentioned formula (1) may be mentioned ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, ((1R,3S)-3-isopropyl-3-{[3-(trifluoromethyl)-7,8-dihydro-1,6-naphthyridin-6(5H)-yl]carbonyl}cyclopentyl) [(3R,4S)-3-methoxytetrahydro-2H-pyran-4-yl]amine, ((1R,3S)-3-isopropyl-3-{[3-(trifluoromethyl)-7,8-dihydro-1,6-naphthyridin-6(5H)-yl]carbonyl}cyclopentyl) [(3R,4R)-3-methoxytetrahydro-2H-pyran-4-yl]amine, ((1R,3S)-3-isopropyl-3-{[3-(trifluoromethyl)-7,8-dihydro-1,6-naphthyridin-6(5H)-yl]carbonyl}cyclopentyl)[(3S,4R)-3-methoxytetrahydro-2H-pyran-4-yl]amine, ((1R,3R)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, ((1R,3R)-3-isopropyl-3-{[3-(trifluoromethyl)-7,8-dihydro-1,6-naphthyridin-6(5H)-yl]carbonyl}cyclopentyl)[(3R,4S)-3-methoxytetrahydro-2H-pyran-4-yl]amine, ((1R,3R)-3-isopropyl-3-{[3-(trifluoromethyl)-7,8-dihydro-1,6-naphthyridin-6(5H)-yl]carbonyl}cyclopentyl)[(3R,4R)-3-methoxytetrahydro-2H-pyran-4-yl]amine, ((1R,3R)-3-isopropyl-3-{[3-(trifluoromethyl)-7,8-dihydro-1,6-naphthyridin-6(5H)-yl]carbonyl}cyclopentyl)[(3S,4R)-3-methoxytetrahydro-2H-pyran-4-yl]amine, ((1S,3R)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, ((1S,3R)-3-isopropyl-3-{[3-(trifluoromethyl)-7,8-dihydro-1,6-naphthyridin-6(5H)-yl]carbonyl}cyclopentyl) [(3R,4S)-3-methoxytetrahydro-2H-pyran-4-yl]amine, ((1S,3R)-3-isopropyl-3-{[3-(trifluoromethyl)-7,8-dihydro-1,6-naphthyridin-6(5H)-yl]carbonyl}cyclopentyl)[(3R,4R)-3-methoxytetrahydro-2H-pyran-4-yl]amine, ((1S,3R)-3-isopropyl-3-{[3-(trifluoromethyl)-7,8-dihydro-1,6-naphthyridin-6(5H)-yl]carbonyl}cyclopentyl)[(3S,4R)-3-methoxytetrahydro-2H-pyran-4-yl]amine, ((1S,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine, ((1S,3S)-3-isopropyl-3-{[3-(trifluoromethyl)-7,8-dihydro-1,6-naphthyridin-6(5H)-yl]carbonyl}cyclopentyl)[(3R,4S)-3-methoxytetrahydro-2H-pyran-4-yl]amine, ((1S,3S)-3-isopropyl-3-{[3-(trifluoromethyl)-7,8-dihydro-1,6-naphthyridin-6(5H)-yl]carbonyl}cyclopentyl)[(3R,4R)-3-methoxytetrahydro-2H-pyran-4-yl]amine, and ((1S,3S)-3-isopropyl-3-{[3-(trifluoromethyl)-7,8-dihydro-1,6-naphthyridin-6(5H)-yl]carbonyl}cyclopentyl)[(3S,4R)-3-methoxytetrahydro-2H-pyran-4-yl]amine.

The compound contained in the prophylactic or therapeutic agent for the posterior ocular disease of the present invention is preferably a compound represented by the formula (1a):

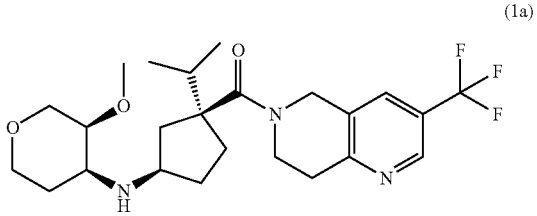 [SMILES: CO[C@@H]1COCC[C@@H]1N[C@@H]1CC[C@@](C(=O)N2CCc3ncc(C(F)(F)F)cc3C2)(C(C)C)C1]

(1a)

or a pharmaceutically acceptable salt.

In the following, the compound represented by the above-mentioned formula (1a) or its pharmaceutically acceptable salt is also referred to as "the compound of the present invention (1a)".

The compound contained in the prophylactic or therapeutic agent for the posterior ocular disease of the present invention is particularly preferably a compound represented by the formula (1b):

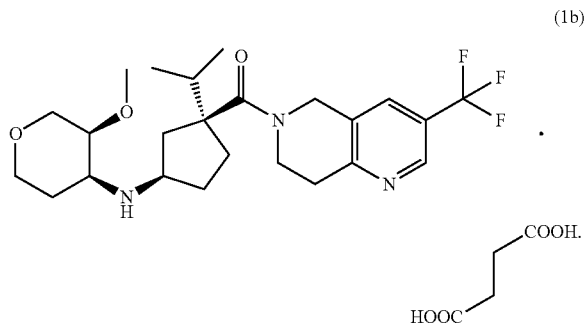

(1b)

The compound represented by the above-mentioned formula (1b) is a succinate of the compound represented by the formula (1a), and this is also referred to as "the compound of the present invention (1b)".

Incidentally, the compound represented by the formula (1b) is also referred to as ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine succinate.

Incidentally, in the following, the compound represented by the formula (1) or the formula (1a) or their salts, and the compound represented by the formula (1b) are totally called to as "the compounds of the present invention".

In the present invention, the posterior ocular disease means a disease at the vitreous body, the retina, the choroid, the sclera or the optic nerve. The posterior ocular disease may be mentioned, for example, a posterior ocular disease to which a CCR2 receptor pertains. In addition, the posterior ocular disease is preferably at least one selected from the group consisting of age-related macular degeneration, diabetic retinopathy, diabetic macular edema, retinal pigmentary degeneration, proliferative vitreoretinopathy, retinal artery occlusion, retinal vein occlusion, uveitis, Leber's disease, retinopathy of prematurity, retinal detachment, retinal pigment epithelial detachment, central serous chorioretinopathy, central exudative chorioretinopathy, polypoidal choroidal vasculopathy, multiple choroiditis, neovascular maculopathy, retinal aneurysm, retinal angiomatous proliferation, ophthalmic nerve disorder caused by these diseases, ophthalmic nerve disorder caused by glaucoma and ischemic ophthalmic nerve disorder, particularly preferably at least one selected from the group consisting of age-related macular degeneration, diabetic retinopathy, diabetic macular edema, retinal vein occlusion and uveitis.

The compounds of the present invention can be formulated into a preparation by adding, if necessary, a pharmaceutically acceptable additive and using a generally employed technique for a single preparation or a formulated preparation.

Also, the prophylactic or therapeutic agent for a posterior ocular disease of the present invention may contain an active ingredient other than the compounds of the present invention. It is an embodiment that an angiotensin receptor blocker is not contained, and it is also an embodiment that it contains the compound of the present invention as sole effective ingredient.

When the compound of the present invention is used for the treatment of the posterior ocular disease, it may be administered to the patient orally or parenterally, and as the administration form, there may be mentioned oral administration, topical administration to eyes (instillation administration, administration to the interior of the conjunctival sac, intravitreal administration, subconjunctival administration, administration under the Tenon's capsule, etc.), intravenous administration, percutaneous administration, etc. The preferred dosage form to be used for topically administering the compounds of the present invention to eyes may be used eye drops or ophthalmic ointments, or else, injections, in particular, a subconjunctival administration agent, a Tenon's capsule administration agent or an intravitreal administration agent is used. The preparation containing the compounds of the present invention as an active ingredient is formulated into a dosage form suitable for administration with a pharmaceutically acceptable additive(s), if necessary.

The dosage form suitable for the oral administration may be mentioned, for example, tablets, capsules, granules, powders, etc., and the dosage form suitable for parenteral administration may be mentioned, for example, injections, eye drops, ophthalmic ointments, plasters, gels, intercalating agents, etc. These can be prepared by using usual techniques generally used in the field of the art. Moreover, in order to take advantage of the sustained action of the therapeutic effect of the present invention more effectively, it may be made a preparation for intraocular implant or a preparation which is made like DDS such as a microsphere, etc.

For example, the tablet can be prepared by optionally selecting and using an excipient, a disintegrator, a binder, a lubricant, a coating agent, a corrigent, etc. The excipient may be mentioned, for example, lactose, glucose, D-mannitol, anhydrous dibasic calcium phosphate, starch, sucrose, etc. The disintegrator may be mentioned, for example, carboxymethyl cellulose, calcium carboxymethyl cellulose, croscarmellose sodium, crospovidone, starch, partially pregelatinized starch, low-substituted hydroxypropyl cellulose, etc. The binder may be mentioned, for example, hydroxypropyl cellulose, ethyl cellulose, gum Arabic, starch, partially pregelatinized starch, polyvinyl pyrrolidone, polyvinyl alcohol, etc. The lubricant may be mentioned, for example, magnesium stearate, calcium stearate, talc, hydrated silicon dioxide, hydrogenated oil, etc. The coating agent may be mentioned, for example, refined white sugar, hydroxypropylmethyl cellulose, hydroxypropyl cellulose, methyl cellulose, ethyl cellulose, polyvinyl pyrrolidone, etc. The corrigent may be mentioned, for example, citric acid, aspartame, ascorbic acid, menthol, etc.

The injection can be prepared by selecting and using an isotonicifier, a buffering agent, a surfactant, a thickener, etc., depending on necessity. The isotonicifier may be mentioned, for example, sodium chloride, etc. The buffering agent may be mentioned, for example, sodium phosphate, etc. The surfactant may be mentioned, for example, polyoxyethylene sorbitan monooleate, etc. The thickener may be mentioned, for example, methyl cellulose, etc.

The eye drop can be prepared by selecting and using an isotonicifier, a buffering agent, a surfactant, a stabilizer, an antiseptic, etc., depending on necessity, and a pH of which may be within the range acceptable for an ophthalmic preparation, it is usually preferred in the range of 4 to 8. The isotonicifier may be mentioned, for example, sodium chloride, concentrated glycerin, etc. The buffering agent may be mentioned, for example, sodium phosphate, sodium acetate, etc. The surfactant may be mentioned, polyoxyethylene sorbitan monooleate, polyoxyl 40 stearate, polyoxyethylene hardened castor oil, etc. The stabilizer may be mentioned, for example, sodium citrate, sodium edetate, etc. The antiseptic may be mentioned, for example, benzalkonium chloride, paraben, etc.

The ophthalmic ointment can be prepared by using a base generally used such as white petrolatum, liquid paraffin, etc.

The intercalating agent can be prepared by pulverizing and mixing a biodegradable polymer, for example, hydroxypropyl cellulose, hydroxypropylmethyl cellulose, carboxyvinyl polymer, polyacrylic acid, etc., with the present compound, and compression-molding the powder, and if necessary, an excipient, a binder, a stabilizer and/or a pH adjuster may be used.

The preparation for intraocular implant can be prepared by using a biodegradable polymer, for example, a polylactic acid, a polyglycolic acid, a lactic acid-glycolic acid copolymer, a hydroxypropyl cellulose, etc.

An administration dose of the compounds of the present invention may be optionally changed depending on a dosage form, severity of the symptoms, an age, a body weight or a volume of eye balls of a patient to be administered, and a judgment of a doctor, etc., and in the case of the oral administration, it can be generally administered to an adult person per a day of 0.01 to 10,000 mg, preferably 0.1 to 5,000 mg, more preferably 0.5 to 2,500 mg once or divided into several times, in the case of the injection, it can be generally administered to an adult person of 0.0001 to 2,000 mg once or divided into several times. In addition, in the case of the eye drops or the intercalating agent, it can be administered a material having a concentration of an active ingredient of 0.000001 to 10% (w/v), preferably 0.00001 to 1% (w/v), more preferably 0.0001 to 0.1% (w/v) once a day or divided into several times. Moreover, in the case of the plasters, the plaster containing 0.0001 to 2,000 mg can be patched to an adult person, and in the case of the preparation for intraocular implant, the preparation for intraocular implant containing 0.0001 to 2,000 mg can be implanted into eyes to an adult person.

EXAMPLES

In the following, the results of Pharmacological tests and Preparation examples are shown, and these examples are intended to better understand the present invention and not to limit the scope of the present invention.

[Pharmacological Test 1]

By using a laser-induced rat choroidal neovascularization model (Invest. Ophthalmol. Vis. Sci., 40(2), 459-466 (1999)), usefulness of the compounds of the present invention was evaluated.

(Preparation Method of Krypton Laser-Induced Rat Choroidal Neovascularization Model Animal)

A rat was intramuscularly administered 1 ml/kg of a mixed solution (7:1) comprising a 5% (W/V) ketamine hydrochloride injection solution and a 2% xylazine hydrochloride injection solution to perform general anesthesia, and after a 0.5% (W/V) tropicamide-0.5% phenylephrine hydrochloride eye drop was dropped into eyes to perform mydriasis, photocoagulation was carried out by a krypton laser photocoagulation apparatus. The photocoagulation was carried out at the posterior part of eye ground, while avoiding thick retinal blood vessels, by focusing on the deep retina with eight spots per an eye in a scattered state (coagulation conditions: spot size 100 μm, output 100 mW, coagulation time 0.1 second). After the photocoagulation, the ocular fundus was photographed to confirm laser irradiated sites.

(Test Compound)

In the present pharmacological test, as the compounds of the present invention, a compound (in the following, the used compound is also called to as "Compound A") prepared in accordance with the synthetic methods disclosed in WO 2003/092586A and WO 2005/044264A was used.

Compound A is a compound represented by the formula (A):

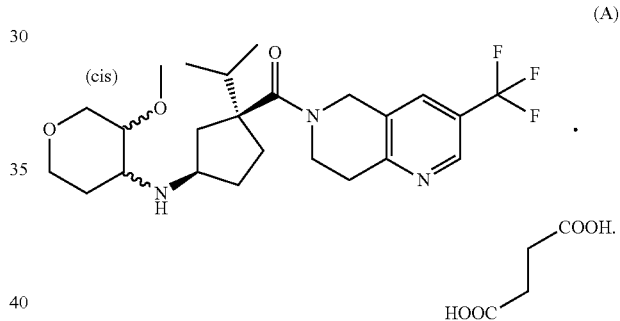

(A)

That is, Compound (A) is a diastereomer mixture of ((1R,3S)-3-isopropyl-3-{[3-(trifluoromethyl)-7,8-dihydro-1,6-naphthyridin-6(5H)-yl]carbonyl}cyclopentyl)[(3S,4S)-3-methoxytetrahydro-2H-pyran-4-yl]amine succinate, the compound represented by the formula (1b):

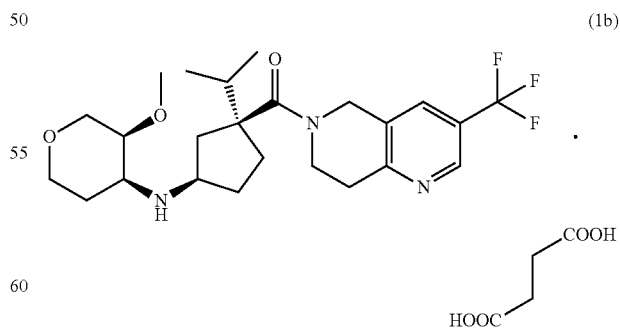

(1b)

and ((1R,3S)-3-isopropyl-3-{[3-(trifluoromethyl)-7,8-dihydro-1,6-naphthyridin-6(5H)-yl]carbonyl}cyclopentyl) [(3R,4R)-3-methoxytetrahydro-2H-pyran-4-yl]amine succinate, the compound represented by the formula (1b'):

[Formula 10]

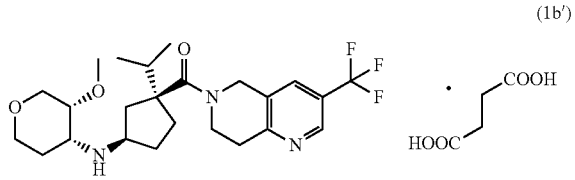

(1b')

with a mixing ratio of 1:1.

(Drug Administration Method)

Compound A was mixed with a 1% (W/V) methyl cellulose solution (prepared by dissolving methyl cellulose in purified water) so that it became 0.4, 1.2, 4 and 12 mg/ml, and an administration solution containing Compound A was orally administered twice a day for 7 days from the surgery day including the surgery day of the photocoagulation with a dose of 2, 6, 20 and 60 mg/kg. Incidentally, to the base administered group was similarly administered a 1% (W/V) methyl cellulose solution.

(Evaluation Method)

At the $7^{th}$ day after the photocoagulation, a rat was intramuscularly administered 1 ml/kg of a mixed solution (7:1) comprising a 5% (W/V) ketamine hydrochloride injection solution and a 2% xylazine hydrochloride injection solution to perform general anesthesia, and a 0.5% (W/V) tropicamide-0.5% phenylephrine hydrochloride eye drop was dropped into eyes to perform mydriasis, 0.1 ml of a 10% fluorescein solution was injected into a vein of penis to carry out fluorescein fundus angiography. A spot from which no leakage of fluorescence was admitted by the fluorescein fundus angiography was judged as negative (no neovascularization), and a spot from which leakage of fluorescence was admitted was judged as positive. In addition, when the photocoagulation portions from which a slight leakage of fluorescence was admitted were present two portions, it was judged as positive (neovascularization exists). Thereafter, according to Numerical formula 1, a rate of incidence of choroidal neovascularization (%) was calculated from a number of positive spot(s) to the eight spots to which the laser was irradiated, and a suppressing rate (%) of the evaluated drug was calculated in accordance with Numerical formula 2. The results of Compound A are shown in Table 1. Incidentally, a number of the samples of each administered group is 7 or 8.

Rate of incidence of choroidal neovascularization (%)=(Number of positive spot(s)/Number of whole photocoagulation portion)×100    [Numerical formula 1]

Suppressing rate (%)={$(A_0-A_X)/A_0$}×100    [Numerical formula 2]

$A_0$: Rate of incidence of choroidal neovascularization of base administered group $A_X$: Rate of incidence of choroidal neovascularization of drug administered group

TABLE 1

| Group constitution | | Suppressing rate (%) |
|---|---|---|
| Compound A | 2 mg/kg | 32.8 |
| Compound A | 6 mg/kg | 39.5 |
| Compound A | 20 mg/kg | 52.9 |
| Compound A | 60 mg/kg | 62.7 |

As is clear from Table 1, it could be shown that Compound A inhibits choroidal neovascularization in a laser-induced rat choroidal neovascularization model animal. From the results mentioned above, it could be shown that the compounds of the present invention have an excellent angiogenesis inhibitory action at the choroid, and have remarkable prophylaxis or treatment effects on a choroid disease to which neovascularization pertains such as age-related macular degeneration (in particular, exudative age-related macular degeneration).

[Pharmacological Test 2]

Thrombin has been reported to induce thrombogenesis at the retinal blood vessel by intravitreal administration (Journal of Japanese Ophthalmological Society, 1989; 93: 978-985), and generally been used as a model for pathological conditions (for example, diabetic retinopathy, diabetic macular edema, retinal vein occlusion, retinal artery occlusion, etc.) accompanied by retinal angiopathy (vascular occlusion). Thus, by using a rat model of thrombin-induced retinal vascular hyperpermeability usefulness of the compounds of the present invention was evaluated.

(Preparation Method of the Rat Model of Thrombin-Induced Retinal Vascular Hyperpermeability)

A rat was intramuscularly administered 1 ml/kg of a mixed solution (7:1) comprising a 5% (W/V) ketamine hydrochloride injection solution and a 2% xylazine hydrochloride injection solution to perform general anesthesia, and a 0.5% (W/V) tropicamide-0.5% phenylephrine hydrochloride eye drop was dropped into eyes to perform mydriasis. Thereafter, 5 μL of thrombin (600 U/ml) was injected into the vitreous body by using a 32G needle so as not to damage the crystalline lens and the retina. A rat of the normal group was administered PBS (phosphate buffer) in place of thrombin.

(Drug Administration Method)

Compound A was dissolved in a 1% (W/V) methyl cellulose solution (prepared by dissolving methyl cellulose in purified water) so that it became 1.2 mg/ml to prepare a Compound A solution. The Compound A solution was orally administered with a dose of 6 mg/kg, at 30 minutes before, 6 and 20 hours after the intravitreal administration of thrombin. Incidentally, to the base administered group was similarly administered a 1% (W/V) methyl cellulose solution. In addition, N-[4-(3,4-dichlorobenzamido)benzyl]-N, N-dimethyl-N-(tetrahydropyran-4-yl)ammonium chloride (in the following, it is also referred to as "Compound B".) and 2(S)-[1-[3-(3,5-difluorophenyl)-2(E)-propenoyl]piperidin-4-yl]-2-[4-(1H-pyrrolo[2,3-b]pyridin-3-yl)piperidin-1-yl]ethanol (in the following, it is also referred to as "Compound C".) which were CCR2 receptor antagonists used for comparison were each synthesized according to the synthetic methods described in WO 2009/055516A and Bioorg. Med. Chem. Lett. 2008; 18: 6468, respectively. Compound B and Compound C were each mixed with a phosphate buffer containing 5% Cremophor and 10% dimethylsulfoxide, respectively, and then, intraperitoneally administered.

(Evaluation Method)

After 24 hours from intravitreal administration of thrombin, the rat was euthanized by exsanguination, and then, the eyeballs of the rat were excised so as not to mix with blood. After extraction of the eyeballs, the vitreous body was rapidly collected by making a tiny cut at around the optic papilla using a scalpel. The collected vitreous body was optionally diluted by purified water, and the protein concentration was measured by the Bradford method. The protein concentration of the vitreous body thus measured was used as an index of the retinal vascular permeability.

Thereafter, according to the Numerical formula 3, a suppressing rate (%) of the evaluated drug against the retinal vascular hyperpermeability caused by thrombin was calculated. The results of Compound A, B and C are shown in Table 2. Incidentally, a number of the samples of each administered group is 7 or 8 per on group, and an average value thereof was used for calculating the suppressing rate.

Retinal vascular permeability suppressing rate (%)=
{(PY-PZ)/(PY-PX)}×100        [Numerical formula 3]

PX: Protein concentration in vitreous body of Normal group (untreated)
PY: Protein concentration in vitreous body of thrombin intravitreally administered+base administered group
PZ: Protein concentration in vitreous body of thrombin intravitreally administered+drug administered group

TABLE 2

| Group constitution | | Suppressing rate (%) |
|---|---|---|
| Compound A | 6 mg/kg | 15 |
| Compound B | 10 mg/kg | −13 |
| Compound C | 10 mg/kg | −1 |

As is clear from Table 2, it could be shown that Compound A could suppress the retinal vascular hyperpermeability in the rat model of thrombin-induced retinal vascular hyperpermeability. From the results mentioned above, it could be shown that the compounds of the present invention have an excellent suppressing effect against the retinal vascular hyperpermeability, and have remarkable prophylaxis or treatment effects on the posterior ocular diseases such as diabetic retinopathy, diabetic macular edema, etc., which were accompanied by the retinal vascular hyperpermeability.

[Pharmacological Test 3]

TNFα is a cytokine which has been reported to increase its expression in proliferative diabetic retinopathy or at the vitreous body of retinal vein occlusion (Eye 2006; 20: 1366-1369, Jpn. J. Ophthalmol. 2011; 55: 256-63), and in a streptozocin-induced diabetes model, it has been reported that it participates in onset and progress of diabetic retinopathy through permeability enhancement or histopathological alteration of retinal vessel (Mol. Vis. 2009; 15: 1418-1428). Thus, by using a rat model of TNFα-induced retinal vascular hyperpermeability, usefulness of Compound A, the diastereomer I of Compound A and the diastereomer II of Compound A were evaluated.

(Preparation Method of the Rat Model of TNFα-Induced Retinal Vascular Hyperpermeability)

A rat was intramuscularly administered 1 ml/kg of a mixed solution (7:1) comprising a 5% (W/V) ketamine hydrochloride injection solution and a 2% xylazine hydrochloride injection solution to perform general anesthesia, and a 0.5% (W/V) tropicamide-0.5% phenylephrine hydrochloride eye drop was dropped into eyes to perform mydriasis. Thereafter, 5 μL of TNFα (10 μg/ml) was injected into the vitreous body by using a 32G needle so as not to damage the crystalline lens and the retina. A rat of normal group was administered PBS (phosphate buffer) in place of the TNFα.

(Drug Administration Method)

Compound A was dissolved in a 1% (W/V) methyl cellulose solution (prepared by dissolving methyl cellulose in purified water) so that it became 2 and 20 mg/ml to prepare a Compound A solution. The Compound A solution was orally administered with a dose of 10 and 100 mg/kg at 30 minutes before, 6 and 20 hours after administration of TNFα in the vitreous body. The diastereomer I of Compound A and the diastereomer II of Compound A were also similarly prepared and administered. Incidentally, the base administered group was similarly administered a 1% (W/V) methyl cellulose solution.

In addition, RS-504393 which is a CCR2 receptor antagonist was used those purchased from Tocris Bioscience Inc., and orally administered in the same manner with a dose of 3 and 30 mg/kg.

(Evaluation Method)

After 24 hours from administration of TNFα in the vitreous body, the rat was euthanized by exsanguination, and then, the eyeballs of the rat were excised so as not to mix with a blood. After extraction of the eyeballs, the vitreous body was rapidly collected by making a tiny cut at around the optic papilla using a surgical scalpel. The collected vitreous body was optionally diluted by purified water, and the protein concentration was measured by the Bradford method. The protein concentration of the vitreous body thus measured was used as an index of the retinal vascular permeability. Thereafter, according to Numerical formula 4, a suppressing rate (%) of the evaluated drug against the retinal vascular hyperpermeability caused by TNFα was calculated. The results of Compound A, the diastereomer I of Compound A, the diastereomer II of Compound A and RS-504393 are shown in Table 3. Incidentally, a number of the samples of each administered group is 7 or 8 per one group, and an average value thereof was used for calculating the suppressing rate.

Retinal vascular permeability suppressing rate (%)=
{(PY-PZ)/(PY-PX)}×100        [Numerical formula 4]

PX: Protein concentration in the vitreous body of Normal group (untreated)
PY: Protein concentration in the vitreous body of TNFα intravitreally administered+base administered group
PZ: Protein concentration in the vitreous body of TNFα intravitreally administered+Drug administered group

TABLE 3

| Group constitution | | Suppressing rate (%) |
|---|---|---|
| Compound A | 10 mg/kg | 63 |
| | 100 mg/kg | 88 |
| Diastereomer I of Compound A | 10 mg/kg | 70 |
| | 100 mg/kg | 81 |
| Diastereomer II of Compound A | 10 mg/kg | 54 |
| | 100 mg/kg | 84 |
| RS-504393 | 3 mg/kg | 18 |
| | 30 mg/kg | −13 |

As is clear from Table 3, it could be shown that Compound A, diastereomer I of Compound A and diastereomer II of Compound A could suppress the retinal vascular hyperpermeability in the rat model of TNFα-induced retinal vascular hyperpermeability. From the results mentioned above, it could be shown that the compounds of the present invention have excellent suppressing effect against the retinal vascular hyperpermeability, and have remarkable prophylaxis or treatment effects on the posterior ocular disease such as diabetic retinopathy, diabetic macular edema, etc., which were accompanied by the retinal vascular hyperpermeability.

Incidentally, the diastereomer I of Compound A and the diastereomer II of Compound A were synthesized in accordance with the synthetic method described in WO 2003/

092586A and WO 2005/044264A. A retention time of the diastereomer I of Compound A was 6.6 minutes, and a retention time of the diastereomer II of Compound A was 10.9 minutes by the analytical conditions shown below.

<Analytical Conditions>

Column: Chiralpak AD-H (4.6×250 mm)

Mobile phase: (0.1% Isopropylamine in Hexane): EtOH=80:20

Flow rate: 1.0 mL/min

UV: 215 nm

Temperature: 25° C.

[Pharmacological Test 4]

To investigate an effectiveness of Compound A by topical administration, the effect of intravitreal administration of Compound A on a rat model of TNFα-induced retinal vascular hyperpermeability was investigated.

(Preparation Method of the Rat Model of TNFα-Induced Retinal Vascular Hyperpermeability)

A model was prepared in the same manner as in Pharmacological test 3.

(Drug administration Method)

Compound A was dissolved in a mixed solution of dimethylsulfoxide and PLA0020 with a ratio of 4:1 so that it became 40 mg/ml to prepare a solution of Compound A. Immediately after intravitreal administration of TNFα, the solution of Compound A was intravitreally administered with a dose of 100 μg/eyes. Incidentally, to the base administered group, a mixed solution of dimethylsulfoxide and PLA0020 with a ratio of 4:1 was similarly administered.

(Evaluation Method)

After 24 hours from intravitreal administration of TNFα, the rat was euthanized by exsanguination, and then, the eyeballs of the rat were excised so as not to mix with a blood. After extraction of the eyeballs, the vitreous body was rapidly collected by making a tiny cut at around the optic papilla using a surgical scalpel. The collected vitreous body was optionally diluted by purified water, and the protein concentration was measured by the Bradford method. The protein concentration of the vitreous body thus measured was used as an index of the retinal vascular permeability. Thereafter, according to Numerical formula 4, a suppressing rate (%) of the evaluated drug against the retinal vascular hyperpermeability caused by TNFα was calculated. The results of Compound A are shown in Table 4. Incidentally, a number of the samples of each administered group is 7 per one group, and an average value thereof was used for calculating the suppressing rate.

TABLE 4

| Group constitution | | Suppressing rate (%) |
|---|---|---|
| Compound A | 100 μg/eye | 61 |

As is clear from Table 4, it could be shown that Compound A could suppress the retinal vascular hyperpermeability by intravitreal administration in the rat model of TNFα-induced retinal vascular hyperpermeability. From the results mentioned above, it could be shown that the compounds of the present invention were effective against the retinal disease not only by whole body administration, but also by topical administration to eyes.

PREPARATION EXAMPLES

The drugs of the present invention are more specifically explained by referring to Preparation examples, but the present invention is not limited by these Preparation examples alone.

Prescription Example 1

Ophthalmic Solution

In 100 ml
Compound of the present invention: 10 mg
Sodium chloride: 900 mg
Polysorbate 80: Suitable amount
Disodium hydrogen phosphate: Suitable amount
Sodium dihydrogen phosphate: Suitable amount
Sterile purified water: Suitable amount The compound of the present invention and the other above-mentioned components are added to sterile purified water, and these are thoroughly mixed to prepare an eye drop. By changing the amount to be added of the compound of the present invention, an eye drop with a concentration of 0.05% (w/v) to 1% (w/v) can be prepared.

Prescription Example 2

Ophthalmic Ointment

In 100 g
Compound of the present invention: 0.3 g
Liquid paraffin: 10.0 g
White petrolatum: Suitable amount The compound of the present invention is added to uniformly melt white petrolatum and liquid paraffin, and after thoroughly mixing them, they are gradually cooled to prepare an ophthalmic ointment. By changing the amount to be added of the compound of the present invention, an ophthalmic ointment with a concentration of 0.05% (w/v) to 1% (w/w) can be prepared.

Prescription Example 3

Tablet

In 100 mg
Compound of the present invention: 1 mg
Lactose: 66.4 mg
Corn starch: 20 mg
Calcium carboxymethyl cellulose: 6 mg
Hydroxypropyl cellulose: 6 mg
Magnesium stearate: 0.6 mg The compound of the present invention and lactose are mixed in a mixer, calcium carboxymethyl cellulose and hydroxypropyl cellulose are added to the mixture and the resulting mixture is granulated. The obtained granules are dried, then, adjusted the granule size, and magnesium stearate is added to the adjusted granules and the resulting mixture is tableted by a tableting machine. Also, by optionally changing the amounts to be added of the compound of the present invention, calcium carboxymethyl cellulose and hydroxypropyl cellulose, a tablet with a content of 0.1 mg to 50 mg of the compound of the present invention in 100 mg can be prepared.

Prescription Example 4

Injection or Intravitreal Administration Agent

In 10 ml
Compound of the present invention: 10 mg
Sodium chloride: 90 mg
Polysorbate 80: Suitable amount
Sterile purified water: Suitable amount The compound of the present invention and the other above-mentioned components are added to sterile purified water, and these are thoroughly mixed and dissolved or suspended to prepare an injection. By optionally changing the amounts to be added of the compound of the present invention and the other above-mentioned components, an injection with a content of 2 mg to 200 mg of the compound of the present invention in 10 ml can be prepared. The thus prepared injection can be administered as an injection for an ocular administration, for example, as an intravitreal administration agent.

The invention claimed is:

1. A method for treating a posterior ocular disease in a human subject, the method comprising administering to the human subject a therapeutically effective amount of a compound represented by the formula (1):

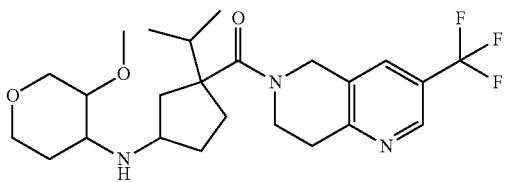

(1)

its enantiomer or diastereomer, or a pharmaceutically acceptable salt thereof as an active ingredient, wherein the posterior ocular disease is at least one selected from the group consisting of age-related macular degeneration, diabetic retinopathy, diabetic macular edema, retinal vein occlusion and uveitis.

2. The method according to claim 1, wherein the compound represented by the formula (1) is a compound represented by the formula (1a):

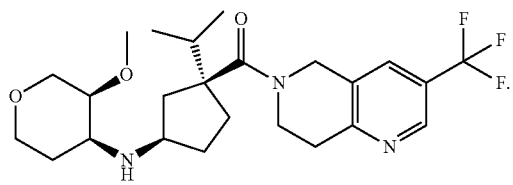

(1a)

3. The method according to claim 1, wherein the pharmaceutically acceptable salt of the compound represented by the formula (1) is a succinate.

4. The method according to claim 1, wherein the posterior ocular disease is a disease at a vitreous body, a retina, a choroid, a sclera or an optic nerve.

5. The method according to claim 1, wherein the posterior ocular disease is a posterior ocular disease to which a CCR2 receptor pertains.

* * * * *